(12) United States Patent
Abe et al.

(10) Patent No.: US 8,580,429 B2
(45) Date of Patent: *Nov. 12, 2013

(54) NON-AQUEOUS ELECTROLYTE FOR A LITHIUM BATTERY, LITHIUM BATTERY WHEREIN SAID ELECTROLYTE IS USED, AND HYDROXY-ACID DERIVATIVE FOR USE IN SAID ELECTROLYTE

(75) Inventors: Koji Abe, Yamaguchi (JP); Kazuyuki Kawabe, Yamaguchi (JP)

(73) Assignee: Ube Industries, Ltd., Ube-shi (JP)

( * ) Notice: Subject to any disclaimer, the term of this patent is extended or adjusted under 35 U.S.C. 154(b) by 460 days.

This patent is subject to a terminal disclaimer.

(21) Appl. No.: 12/921,894

(22) PCT Filed: Mar. 10, 2009

(86) PCT No.: PCT/JP2009/054553
§ 371 (c)(1),
(2), (4) Date: Nov. 30, 2010

(87) PCT Pub. No.: WO2009/113545
PCT Pub. Date: Sep. 17, 2009

(65) Prior Publication Data
US 2011/0064998 A1 Mar. 17, 2011

(30) Foreign Application Priority Data
Mar. 13, 2008 (JP) .................................. 2008-064629

(51) Int. Cl.
*H01M 6/14* (2006.01)
(52) U.S. Cl.
USPC ........... 429/200; 429/330; 429/332; 429/335; 429/307; 429/231.1; 429/231.3; 429/231.6; 429/231.4; 429/231.8; 429/218.1; 252/62.2
(58) Field of Classification Search
USPC .............. 429/200, 330, 332, 335, 307, 231.1, 429/231.3, 231.6, 231.4, 231.8, 218.1; 252/62.2
See application file for complete search history.

(56) References Cited

U.S. PATENT DOCUMENTS

| | | | |
|---|---|---|---|
| 5,284,722 A | 2/1994 | Sugeno | |
| 6,210,834 B1 * | 4/2001 | Kweon et al. .............. | 429/231.3 |
| 2004/0058251 A1 | 3/2004 | Hamamoto et al. | |
| 2005/0118512 A1 * | 6/2005 | Onuki et al. ................. | 429/340 |
| 2008/0038644 A1 | 2/2008 | Abe et al. | |
| 2008/0102377 A1 | 5/2008 | Abe et al. | |
| 2009/0309060 A1 | 12/2009 | Oka et al. | |

FOREIGN PATENT DOCUMENTS

| | | |
|---|---|---|
| JP | 7-78634 A | 3/1995 |
| JP | 7-320777 A | 12/1995 |
| JP | 2000 223153 | 8/2000 |
| JP | 2000 331709 | 11/2000 |
| WO | 02 15319 | 2/2002 |
| WO | 2005 122318 | 12/2005 |
| WO | 2006 070546 | 7/2006 |
| WO | WO 2008/001955 A1 | 1/2008 |

OTHER PUBLICATIONS

Extended European Search Report issued Nov. 5, 2012 in Patent Application No. 09719795.8.

* cited by examiner

*Primary Examiner* — Laura Weiner
(74) *Attorney, Agent, or Firm* — Oblon, Spivak, McClelland, Maier & Neustadt, L.L.P.

(57) ABSTRACT

Disclosed are (1) a nonaqueous electrolytic solution for lithium battery comprising an electrolyte dissolved in a nonaqueous solvent, which contains at least one hydroxy acid derivative compound represented by the formulae (I) and (II) in an amount of from 0.01 to 10% by mass of the nonaqueous electrolytic solution, and which can improve the low-temperature and high-temperature cycle property thereof (wherein $R^1$ represents an alkyl group having from 1 to 6 carbon atoms, an alkenyl group having from 2 to 6 carbon atoms, or an alkynyl group having from 3 to 6 carbon atoms, $R^2$ represents a sulfonyl group or a formyl group, $R^3$ and $R^4$ each represent a hydrogen atom or a methyl group); (2) a lithium battery comprising a positive electrode, a negative electrode and a nonaqueous electrolytic solution of an electrolyte salt dissolved in a nonaqueous solvent, wherein the nonaqueous electrolytic solution contains at least one hydroxy acid derivative compound represented by the above formulae (I) and (II) in an amount of from 0.01 to 10% by mass of the nonaqueous electrolytic solution; and (3) a hydroxy acid derivative compound represented by the following formula (III) or (IV) (wherein $R^6$ represents an alkenyl group having from 2 to 6 carbon atoms, or an alkynyl group having from 3 to 6 carbon atoms, $R^7$ represents a sulfonyl group or a formyl group, and $R^8$ and $R^9$ each represent a hydrogen atom or a methyl group).

13 Claims, No Drawings

NON-AQUEOUS ELECTROLYTE FOR A LITHIUM BATTERY, LITHIUM BATTERY WHEREIN SAID ELECTROLYTE IS USED, AND HYDROXY-ACID DERIVATIVE FOR USE IN SAID ELECTROLYTE

TECHNICAL FIELD

The present invention relates to a nonaqueous electrolytic solution for lithium battery capable of improving the low-temperature and high-temperature cycle property thereof, to a lithium battery using the same, and to a novel hydroxy acid derivative compound usable for lithium batteries, etc.

BACKGROUND ART

In recent years, lithium secondary batteries have been widely used as power supplies for small-size electronic devices such as mobile telephones, notebook-size personal computers and the like, and for electric vehicles as well as for electric power storage, etc. These electronic devices and vehicles may be used in abroad temperature range, for example, at midsummer high temperatures or at frigid low temperatures, and are therefore required to have a well-balanced charge-discharge cycle property in a broad temperature range.

A lithium secondary battery is mainly constituted of a positive electrode and a negative electrode containing a material capable of absorbing and releasing lithium, and a nonaqueous electrolytic solution containing a lithium salt and a nonaqueous solvent. As the nonaqueous solvent, used are carbonates such as ethylene carbonate (EC), propylene carbonate (PC), etc.

As the negative electrode, known are metal lithium, and metal compounds (metal elemental substances, oxides, alloys with lithium, etc.) and carbon materials capable of absorbing and releasing lithium. In particular, lithium secondary batteries using a carbon material capable of absorbing and releasing lithium such as coke, artificial graphite, natural graphite or the like have been widely put into practical use.

For example, it is known that, in the lithium secondary battery using a highly-crystalline carbon material such as artificial graphite, natural graphite or the like as the negative electrode material, the decomposed product or gas generated through reductive decomposition of the solvent in the non-aqueous electrolytic solution on the surface of the negative electrode during charging detracts from the electrochemical reaction favorable for the battery, therefore worsening the cycle property of the battery. Deposition of the decomposed product of the nonaqueous solvent interferes with smooth absorption and release of lithium by the negative electrode, and therefore, in particular, the cycle property at low temperatures and at high temperatures may be thereby often worsened.

In addition, it is known that a lithium secondary battery using a lithium metal or its alloy, or a metal elemental substance such as tin, silicon or the like or its metal oxide as the negative electrode material may have a high initial battery capacity but its battery performance such as battery capacity and cycle property greatly worsens, since the micronized powdering of the material is promoted during cycles thereby bringing about accelerated reductive decomposition of the nonaqueous solvent, as compared with the negative electrode of a carbon material. In addition, the micronized powdering of the negative electrode material and the deposition of the decomposed product of the nonaqueous solvent may interfere with smooth absorption and release of lithium by the negative electrode, and therefore, in particular, the cycle property at low temperatures and high temperatures may be thereby often worsened.

On the other hand, it is known that, in a lithium secondary battery using, for example, $LiCoO_2$, $LiMn_2O_4$, $LiNiO_2$, $LiFePO_4$ or the like as the positive electrode, when the non-aqueous solvent in the nonaqueous electrolytic solution is heated at a high temperature in the charged state, the decomposed product or gas thereby locally generated through partial oxidative decomposition in the interface between the positive electrode material and the nonaqueous electrolytic solution interferes with the electrochemical reaction favorable for the battery, and therefore the battery performance such as cycle property is thereby also worsened.

As in the above, the decomposed product or gas generated through decomposition of the nonaqueous electrolytic solution on the positive electrode or the negative electrode interferes with the movement of lithium ions or swells the battery, and the battery performance is thereby worsened. Despite the situation, electronic appliances equipped with lithium secondary batteries therein are offering more and more an increasing range of functions and are being in a stream of further increase in the power consumption. With that, the capacity of lithium secondary batteries is being much increased, and the space volume for the nonaqueous electrolytic solution in the battery is decreased by increasing the density of the electrode and by reducing the useless space volume in the battery. Accordingly, the situation is that even decomposition of only a small amount of the nonaqueous electrolytic solution may worsen the battery performance at low temperatures and high temperatures.

Patent Reference 1 discloses a lithium secondary battery comprising a positive electrode containing a lithium manganese oxide having a spinel structure, a negative electrode containing a carbon material, and an organic electrolytic solution, wherein the organic electrolytic solution is made to contain from 0.5 to 3.0% of a malonic acid diester to thereby improve the cycle property of the battery at 25° C.

As a lithium primary battery, for example, there is known a lithium primary battery comprising manganese dioxide or graphite fluoride as the positive electrode and a lithium metal as the negative electrode, and this is widely used as having a high energy density. It is desired to inhibit the increase in the internal resistance of the battery during long-term storage and to improve the discharge load characteristic thereof at high temperatures or low temperatures.

Recently, further, as a novel power source for electric vehicles or hybrid electric vehicles, electric storage devices have been developed, for example, an electric double layer capacitor using activated carbon or the like as the electrode from the viewpoint of the output power density thereof, and a so-called hybrid capacitor comprising a combination of the electric storage principle of a lithium ion secondary battery and that of an electric double layer capacitor (an asymmetric capacitor where both the capacity by lithium absorption and release and the electric double layer capacity are utilized) from the viewpoint of both the energy density and the output power density thereof; and it is desired to improve the characteristics, especially the low-temperature and high-temperature cycle property of these capacitors.

[Patent Reference 1] JP-A 2000-223153

DISCLOSURE OF THE INVENTION

Problems that the Invention is to Solve

An object of the present invention is to provide a nonaqueous electrolytic solution for lithium battery capable of improving the low-temperature and high-temperature cycle property thereof, a lithium battery using the same, and a novel hydroxy acid derivative compound usable for lithium batteries, etc.

Means for Solving the Problems

The present inventors have investigated in detail the performance of the nonaqueous electrolytic solutions in the prior art mentioned above. As a result, the current condition is that the nonaqueous electrolytic solution in Patent Reference 1 could not realize a good cycle property in a broad range of low temperatures and high temperatures.

Accordingly, the present inventors have assiduously studied for the purpose of solving the above-mentioned problems and have found that, in a nonaqueous electrolytic solution containing an electrolyte salt dissolved in a nonaqueous solvent, when a hydroxy acid derivative compound where two different substituents of a carboxylate group (—CO$_2$R) and a sulfonyloxy group (—OSO$_2$R) or a formyloxy group (—OCHO) are bonded via a hydrocarbon group is added to the nonaqueous electrolytic solution, then the low-temperature and high-temperature cycle property can be improved, and have completed the present invention.

Specifically, the present invention provides the following (1) to (3):

(1) A nonaqueous electrolytic solution for lithium battery comprising an electrolyte dissolved in a nonaqueous solvent, which contains at least one hydroxy acid derivative compound represented by the following general formulae (I) and (II) in an amount of from 0.01 to 10% by mass of the nonaqueous electrolytic solution:

[Formula 1]

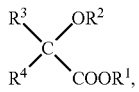

(I)

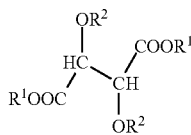

(II)

(In the general formulae (I) and (II), $R^1$ represents a linear or branched alkyl group having from 1 to 6 carbon atoms, a linear or branched alkenyl group having from 2 to 6 carbon atoms, or a linear or branched alkynyl group having from 3 to 6 carbon atoms; $R^2$ represents a sulfonyl group (—SO$_2$R$^5$) (where $R^5$ represents a linear or branched alkyl group having from 1 to 6 carbon atoms, or a linear or branched alkyl group having from 1 to 6 carbon atoms in which at least one hydrogen atom is substituted with a halogen atom), or a formyl group (—CHO); $R^3$ and $R^4$ each represent a hydrogen atom or a methyl group.)

(2) A lithium battery comprising a positive electrode, a negative electrode and a nonaqueous electrolytic solution of an electrolyte salt dissolved in a nonaqueous solvent, wherein the nonaqueous electrolytic solution contains at least one hydroxy acid derivative compound represented by the above-mentioned (I) and (II) in an amount of from 0.01 to 10% by mass of the nonaqueous electrolytic solution.

(3) A hydroxy acid derivative compound represented by the following general formula (III) or (IV):

[Formula 2]

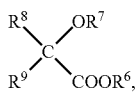

(III)

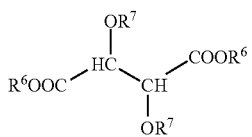

(IV)

(In the general formulae (III) and (IV), $R^6$ represents a linear or branched alkenyl group having from 2 to 6 carbon atoms, or a linear or branched alkynyl group having from 3 to 6 carbon atoms; $R^7$ represents a sulfonyl group) (—SO$_2$R$^{10}$) (where $R^{10}$ represents a linear or branched alkyl group having from 1 to 6 carbon atoms, or a linear or branched alkyl group having from 1 to 6 carbon atoms in which at least one hydrogen atom is substituted with a halogen atom), or a formyl group (—CHO); $R^8$ and $R^9$ each represent a hydrogen atom or a methyl group; provided that, in the general formula (III), when $R^7$ is a sulfonyl group (—SO$_2$R$^{10}$), then $R^6$ is a linear or branched alkenyl group having from 2 to 6 carbon atoms.)

Advantage of the Invention

According to the present invention, there are provided a nonaqueous electrolytic solution for lithium battery capable of improving the low-temperature and high-temperature cycle property thereof, a lithium battery using the same, and a hydroxy acid derivative compound useful as intermediate materials for medicines, agricultural chemicals, electronic materials, polymer materials and the like, and as battery materials.

BEST MODE FOR CARRYING OUT THE INVENTION

The present invention relates to a nonaqueous electrolytic solution for lithium battery, to a lithium battery using the same, and to a novel hydroxy acid derivative compound usable for lithium batteries, etc.

[Nonaqueous Electrolytic Solution]

The nonaqueous electrolytic solution of the present invention is a nonaqueous electrolytic solution of an electrolyte dissolved in a nonaqueous solvent, and is characterized by containing at least one hydroxy acid derivative compound represented by the following general formulae (I) and (II) in an amount of from 0.01 to 10% by mass of the nonaqueous electrolytic solution.

[Formula 3]

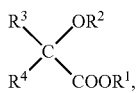

(I)

-continued

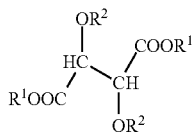
(II)

(In the general formulae (I) and (II), $R^1$ represents a linear or branched alkyl group having from 1 to 6 carbon atoms, a linear or branched alkenyl group having from 2 to 6 carbon atoms, or a linear or branched alkynyl group having from 3 to 6 carbon atoms; $R^2$ represents a sulfonyl group ($-SO_2R^5$) (where $R^5$ represents a linear or branched alkyl group having from 1 to 6 carbon atoms, or a linear or branched alkyl group having from 1 to 6 carbon atoms in which at least one hydrogen atom is substituted with a halogen atom), or a formyl group ($-CHO$); $R^3$ and $R^4$ each represent a hydrogen atom or a methyl group.)

The nonaqueous electrolytic solution of the present invention with a hydroxy acid derivative compound of the general formula (I) or (II) added thereto can improve the low-temperature and high-temperature cycle property thereof. Though not always clear, the reason may be considered as follows:

Specifically, it has been known that, in the hydroxy acid derivative compound in the present invention, two different substituents of a carboxylate group ($-CO_2R^1$) and a sulfonyloxy group ($-OSO_2R^5$) or a formyloxy group ($-OCHO$) are bonded via a hydrocarbon group, and therefore the compound has one reduction potential quite differing from that of a compound having two same substituents. This may be considered because a mixed surface film derived from the two different substituents of the hydroxy acid derivative compound in the present invention may be formed on the electrode, and therefore, the mixed surface film formed at a reduction potential that could not be expected in a case where a compound having two same substituents such as the malonic acid diester described in Patent Reference 1 is used can exhibit the effect of improving the specific, low-temperature and high-temperature cycle property.

In the general formula (I) or (II), the linear or branched alkyl group having from 1 to 6 carbon atoms for the substituent $R^1$ includes a methyl group, an ethyl group, a propyl group, a butyl group, a pentyl group, a hexyl group, a 2-propyl group, etc.

The linear or branched alkenyl group having from 2 to 6 carbon atoms for $R^1$ includes a vinyl group, a 2-propenyl group, a 2-butenyl group, a 3-butenyl group, a 4-pentenyl group, a 2-methyl-2-propenyl group, a 2-methyl-2-butenyl group, a 3-methyl-2-butenyl group, etc.

The linear or branched alkynyl group having from 3 to 6 carbon atoms for $R^1$ includes a 2-propynyl group, a 2-butynyl group, a 3-butynyl group, a 4-pentynyl group, a 5-hexynyl group, a 1-methyl-2-propynyl group, a 1-methyl-2-butynyl group, a 1,1-dimethyl-2-propynyl group, etc.

For the substituent $R^1$, a linear or branched alkenyl group having from 2 to 6 carbon atoms or a linear or branched alkynyl group having from 3 to 6 carbon atoms is preferred to a linear or branched alkyl group having from 1 to 6 carbon atoms; and a linear or branched alkynyl group having from 3 to 6 carbon atoms is most preferred. Of those, preferred are a methyl group, an ethyl group, a vinyl group, a 2-propenyl group, and a 2-propynyl group; more preferred are a vinyl group, a 2-propenyl group, and a 2-propynyl group; and most preferred is a 2-propynyl group [or namely, a propargyl group].

In the general formula (I) or (II), the substituent $R^2$ is preferably a sulfonyl group ($-SO_2R^5$).

The linear or branched alkyl group having from 1 to 6 carbon atoms for the substituent $R^5$ includes a methyl group, an ethyl group, a propyl group, a butyl group, a pentyl group, a hexyl group, a 2-propyl group, etc.

The linear or branched alkyl group having from 1 to 6 carbon atoms, in which at least one hydrogen atom is substituted with a halogen atom, for $R^5$ includes a substituent derived from the above-mentioned, linear or branched alkyl group in which at least one hydrogen atom is substituted with a halogen atom; and its examples include a trifluoromethyl group, and a 2,2,2-trifluoroethyl group. Of those, preferred are a methyl group, an ethyl group, and a trifluoromethyl group; and most preferred is a methyl group.

In the general formula (I), the number of the methyl group of $R^3$ and $R^4$ is preferably 0 ($R^3$ and $R^4$ are both hydrogen atoms) or 1 (any one of $R^3$ and $R^4$ is a methyl group), most preferably 0.

The general formula (I) where the number of the methyl group of $R^3$ and $R^4$ is 1 (any one of $R^3$ and $R^4$ is a methyl group), and the general formula (II) have optical isomers, and all those optical isomers have the same effect.

In the general formulae (I) and (II), the substituents are preferably within the above-mentioned range as capable of enhancing the effect of improving the battery characteristics such as the low-temperature and high-temperature property, etc.

Not specifically defined thereto, examples of the hydroxy acid derivative compound of the general formula (I) or (II) include the following compounds.

The general formula (I) where the number of the methyl group of $R^3$ and $R^4$ is 0 ($R^3$ and $R^4$ are both hydrogen atoms) includes methyl methanesulfonyloxyacetate, ethyl methanesulfonyloxyacetate, vinyl methanesulfonyloxyacetate, 2-propenyl methanesulfonyloxyacetate, 2-propynyl methanesulfonyloxyacetate, methyl formyloxyacetate, ethyl formyloxyacetate, vinyl formyloxyacetate, 2-propenyl formyloxyacetate, 2-propynyl formyloxyacetate, etc.

The general formula (I) where the number of the methyl group of $R^3$ and $R^4$ is 1 (any one of $R^3$ and $R^4$ is a methyl group) includes methyl 2-(methanesulfonyloxy)propionate, ethyl 2-(methanesulfonyloxy)propionate, vinyl 2-(methanesulfonyloxy)propionate, 2-propenyl 2-(methanesulfonyloxy)propionate, 2-propynyl 2-(methanesulfonyloxy)propionate, methyl 2-(formyloxy)propionate, ethyl 2-(formyloxy)propionate, vinyl 2-(formyloxy)propionate, 2-propenyl 2-(formyloxy)propionate, 2-propynyl 2-(formyloxy)propionate, etc.

The general formula (I) where the number of the methyl groups of $R^3$ and $R^4$ is 2 ($R^3$ and $R^4$ are both methyl groups) includes methyl 2-(methanesulfonyloxy)-2-methylpropionate, ethyl 2-(methanesulfonyloxy)-2-methylpropionate, vinyl 2-(methanesulfonyloxy)-2-methylpropionate, 2-propenyl 2-(methanesulfonyloxy)-2-methylpropionate, 2-propynyl 2-(methanesulfonyloxy)-2-methylpropionate, methyl 2-(formyloxy)-2-methylpropionate, ethyl 2-(formyloxy)-2-methylpropionate, vinyl 2-(formyloxy)-2-methylpropionate, 2-propenyl 2-(formyloxy)-2-methylpropionate, 2-propynyl 2-(formyloxy)-2-methylpropionate, etc.

Preferred examples of the hydroxy acid derivative compound of the general formula (I) are one or more selected from methyl methanesulfonyloxyacetate, 2-propenyl methanesulfonyloxyacetate, 2-propynyl methanesulfonyloxyacetate, methyl formyloxyacetate, 2-propenyl formyloxyacetate, 2-propynyl formyloxyacetate, methyl 2-(methanesulfonyloxy)propionate, 2-propenyl 2-(methanesulfonyloxy)propionate, 2-propynyl 2-(methanesulfonyloxy) propionate, methyl 2-(formyloxy)propionate, 2-propenyl 2-(formyloxy)propionate, and 2-propynyl 2-(formyloxy)propionate.

The compound of the general formula (II) includes dimethyl 2,3-di(methanesulfonyloxy)succinate, diethyl 2,3-di(methanesulfonyloxy)succinate, divinyl 2,3-di(methanesulfonyloxy)succinate, di(2-propenyl) 2,3-di(methanesulfonyloxy)succinate, di(2-propynyl) 2,3-di(methanesulfonyloxy)succinate, dimethyl 2,3-di(formyloxy)succinate, diethyl 2,3-di(formyloxy)succinate, divinyl 2,3-di(formyloxy)succinate, di(2-propenyl) 2,3-di(formyloxy)succinate, and di(2-propynyl) 2,3-di(formyloxy)succinate. Of those, preferred are one or more selected from dimethyl 2,3-di(methanesulfonyloxy)succinate, di(2-propenyl) 2,3-di(methanesulfonyloxy)succinate, di(2-propynyl) 2,3-di(methanesulfonyloxy)succinate, dimethyl 2,3-di(formyloxy)succinate, di(2-propenyl) 2,3-di(formyloxy)succinate, and di(2-propynyl) 2,3-di(formyloxy)succinate.

In the nonaqueous electrolytic solution of the present invention, in case where the content of at least one compound selected from the above-mentioned general formulae (I) and (II) to be contained in the nonaqueous electrolytic solution is more than 10% by mass, then an excessive surface film may be formed on the electrode to thereby often lower the low-temperature cycle property of the battery; but when the content is less than 0.01% by mass, then the formation of the surface film may be insufficient and the battery could not enjoy the effect of improving the high-temperature cycle property thereof. Accordingly, the lower limit of the content of the compound is preferably at least 0.01% by mass of the nonaqueous electrolytic solution, more preferably at least 0.1% by mass, even more preferably at least 0.5% by mass, most preferably at least 1% by mass. The upper limit is preferably at most 10% by mass, more preferably at most 7% by mass, even more preferably at most 5% by mass, most preferably at most 3% by mass.

In the nonaqueous electrolytic solution of the present invention, even when the compound of the general formula (I) or (II) is singly therein, the low-temperature and high-temperature cycle property can be improved; however, when the compound is combined therein with a nonaqueous solvent, an electrolyte salt and other additives mentioned below, then the electrolytic solution can exhibit a specific effect of synergistically improving the low-temperature and high-temperature cycle property of the battery. Though not always clear, the reason may be considered because a mixed surface film containing the compound of the general formula (I) or (II) and the constitutive elements of the nonaqueous solvent, the electrolyte salt or the other additives and having a high ionic conductivity may be formed.

[Nonaqueous Solvent]

The nonaqueous solvent for use in the nonaqueous electrolytic solution of the present invention includes cyclic carbonates, linear carbonates, linear esters, ethers, amides, phosphates, sulfones, lactones, nitriles, S=O bond-containing compounds, etc.

The cyclic carbonates include ethylene carbonate (EC), propylene carbonate (PC), butylene carbonate (BC), 4-fluoro-1,3-dioxolan-2-one (FEC), trans or cis-4,5-difluoro-1,3-dioxolan-2-one (the two are collectively referred to as "DFEC"), vinylene carbonate (VC), vinylethylene carbonate (VEC), etc. Of those cyclic carbonates, FEC, DFEC, VC and VEC are preferred as the high-temperature cycle property can be improved; and PC is preferred as the low-temperature cycle property can be improved. In general, EC, FEC, DFEC, VC and VEC may worsen the low-temperature cycle property, but the nonaqueous electrolytic solution containing the hydroxy acid derivative compound of the present invention can improve the low-temperature cycle property.

One type of those solvents may be used, but using two or more different types as combined is preferred as further improving the low-temperature and high-temperature cycle property. Even more preferably, three or more different types are combined. Preferred combinations of the cyclic carbonates include EC and VC; PC and VC; FEC and VC; FEC and EC; FEC and PC; EC, PC and VC; EC, FEC and VC; FEC, PC and VC; FEC, EC, PC and VC; etc.

Not specifically defined, the content of the cyclic carbonate is preferably from 10 to 40% by volume relative to the total volume of the nonaqueous solvent. When the content is less than 10% by volume, then the conductivity of the nonaqueous electrolytic solution may lower, and the low-temperature and high-temperature cycle property may worsen; but when more than 40% by volume, then the viscosity of the nonaqueous electrolytic solution may increase and the low-temperature and high-temperature cycle property may worsen. Accordingly, the above range is preferred.

The linear carbonates include asymmetric linear carbonates such as methyl ethyl carbonate (MEC), methyl propyl carbonate, methyl isopropyl carbonate, methyl butyl carbonate, ethyl propyl carbonate, etc.; symmetric linear carbonates such as dimethyl carbonate (DMC), diethyl carbonate (DEC), dipropyl carbonate, dibutyl carbonate, etc. In particular, the asymmetric carbonates are preferred, as effectively improving the low-temperature cycle property. One type of those solvents may be used, but using two or more different types as combined is preferred as further improving the low-temperature and high-temperature cycle property.

Not specifically defined, the content of the linear carbonate is preferably from 60 to 90% by volume relative to the total volume of the nonaqueous solvent. When the content is less than 60% by volume, then the viscosity of the nonaqueous electrolytic solution may increase and the low-temperature cycle property may worsen; but when more than 90% by volume, then the electric conductivity of the nonaqueous electrolytic solution may lower and the low-temperature and high-temperature cycle property may worsen. Accordingly, the above range is preferred.

The linear esters include methyl propionate, ethyl propionate, methyl acetate, ethyl acetate, methyl pivalate, butyl pivalate, hexyl pivalate, octyl pivalate, dimethyl oxalate, ethyl methyl oxalate, diethyl oxalate, etc. The ethers include tetrahydrofuran, 2-methyltetrahydrofuran, 1,3-dioxane, 1,4-dioxane, 1,2-dimethoxyethane, 1,2-diethoxyethane, 1,2-dibutoxyethane, etc.

The amides include dimethylformamide, etc.; the phosphates include trimethyl phosphate, tributyl phosphate, trioctyl phosphate, etc.; the sulfones include sulfolane, etc.; the lactones include γ-butyrolactone, γ-valerolactone, α-angelicalactone, etc.; the nitriles include acetonitrile, propionitrile, succinonitrile, glutaronitrile, adiponitrile, etc.

The S=O bond-containing compounds include 1,3-propanesultone (PS), ethylene sulfite, hexahydrobenzo[1,3,2]dioxathiolan-2-oxide (this may be referred to also as 1,2-cyclohexanediol cyclic sulfite), 5-vinyl-hexahydro-1,3,2-benzodioxathiol-2-oxide, 1,4-butanediol dimethanesulfonate, 1,3-butanediol dimethanesulfonate, divinyl sulfone, 1,2-bis(vinylsulfonyl)ethane, bis(2-vinylsulfonylethyl)ether, etc.

In general, the S=O bond-containing compounds may worsen the low-temperature cycle property; however, using them as combined with the hydroxy acid derivative compound of the present invention is favorable as improving the low-temperature and high-temperature cycle property. Regarding the content of the S=O bond-containing compound, when the content thereof is more than 10% by mass, then the low-temperature and high-temperature cycle property may worsen; but when less than 0.01% by mass, the effect of improving the low-temperature and high-temperature cycle property could not be sufficiently attained. Accordingly, the content of the S=O bond-containing compound is preferably at least 0.01% by mass of the nonaqueous electrolytic solution, more preferably at least 0.1% by mass, even more preferably at least 0.5% by mass. The upper limit of the content is preferably at most 10% by mass, more preferably at most 5% by mass, even more preferably at most 3% by mass.

In general, the nonaqueous solvents are used as a mixture thereof for attaining the suitable physical properties. Regarding their combinations, for example, there are mentioned a combination of a cyclic carbonate and a linear carbonate, a combination of a cyclic carbonate, a linear carbonate and a lactone, a combination of a cyclic carbonate, a linear carbonate and an ether, a combination of a cyclic carbonate, a linear carbonate and a linear ester, a combination of a cyclic carbonate, a linear carbonate and a nitrile, a combination of a cyclic carbonate, a linear carbonate and an S=O bond-containing compound, etc.

Of those, preferred is using a nonaqueous solvent of a combination of at least a cyclic carbonate and a linear carbonate, as effectively improving the low-temperature and high-temperature cycle property. The ratio of the cyclic carbonate to the linear carbonate is not specifically defined. Preferably, the ratio (by volume) of cyclic carbonate/linear carbonate is from 10/90 to 40/60, more preferably from 15/85 to 35/65, even more preferably from 20/80 to 30/70.

[Electrolyte Salt]

The electrolyte salt for use in the present invention includes lithium salts such as $LiPF_6$, $LiBF_4$, $LiClO_4$, etc.; linear alkyl group—having lithium salts such as $LiN(SO_2CF_3)_2$, $LiN(SO_2C_2F_5)_2$, $LiCF_3SO_3$, $LiC(SO_2CF_3)_3$, $LiPF_4(CF_3)_2$, $LiPF_3(C_2F_5)_3$, $LiPF_3(CF_3)_3$, $LiPF_3(iso-C_3F_7)_3$, $LiPF_5(iso-C_3F_7)$ etc.; cyclic alkylene chain—having lithium salts such as $(CF_2)_2(SO_2)_2NLi$, $(CF_2)_3(SO_2)_2NLi$, etc.; and lithium salts with an anion of an oxalate complex such as lithium bis[oxalate-O,O']borate, lithium difluoro[oxalate-O,O']borate, etc. Of those, especially preferred electrolyte salts are $LiPF_6$, $LiBF_4$, $LiN(SO_2CF_3)_2$, and $LiN(SO_2C_2F_5)_2$; and most preferred electrolyte salts are $LiPF_6$, $LiBF_4$, and $LiN(SO_2CF_3)_2$. One or more of these electrolyte salts may be used herein either singly or as combined.

A preferred combination of these electrolyte salts is a combination containing $LiPF_6$ as combined with at least one selected from $LiBF_4$, $LiN(SO_2CF_3)_2$ and $LiN(SO_2C_2F_5)_2$. Preferred are a combination of $LiPF_6$ and $LiBF_4$; a combination of $LiPF_6$ and $LiN(SO_2CF_3)_2$; a combination of $LiPF_6$ and $LiN(SO_2C_2F_5)_2$, etc.

When the ratio (by mol) of $LiPF_6/[LiBF_4$ or $LiN(SO_2CF_3)_2$ or $LiN(SO_2C_2F_5)_2]$ is smaller than 70/30 in point of the proportion of $LiPF_6$, or when the ratio is larger than 99/1 in point of the proportion of $LiPF_6$, then the low-temperature and high-temperature cycle property may worsen. Accordingly, the ratio (by mol) of $LiPF_6/[LiBF_4$ or $LiN(SO_2CF_3)_2$ or $LiN(SO_2C_2F_5)_2]$ is preferably within a range of from 70/30 to 99/1, more preferably from 80/20 to 98/2. The combination falling within the above range is more effective for bettering the low-temperature and high-temperature cycle property.

The electrolyte salts may be combined in any desired ratio. In the combination of $LiPF_6$ with any of $LiBF_4$, $LiN(SO_2CF_3)_2$ and $LiN(SO_2C_2F_5)_2$, when the proportion (as molar fraction) of the other electrolyte salt than those ingredients to the total electrolyte salts is less than 0.01%, then the effect of improving the low-temperature and high-temperature cycle property may be poor; but when it is more than 45%, then the low-temperature and high-temperature cycle property may worsen. Accordingly, the proportion (as molar fraction) is preferably from 0.01 to 45%, more preferably from 0.03 to 20%, even more preferably from 0.05 to 10%, most preferably from 0.05 to 5%.

The concentration of all these electrolyte salts as dissolved in the solution is generally preferably at least 0.3 M relative to the above-mentioned nonaqueous solvent, more preferably at least 0.5M, most preferably at least 0.7M. The upper limit of the concentration is preferably at most 2.5 M, more preferably at most 2.0 M, even more preferably at most 1.5 M.

As the electrolyte for electric double layer capacitors (condenser), usable are known quaternary ammonium salts such as tetraethylammonium tetrafluoroborate, triethylmethylammonium tetrafluoroborate, tetraethylammonium hexafluorophosphate, etc.

[Other Additives]

An aromatic compound may be added to the nonaqueous electrolytic solution of the present invention, thereby securing the safety of the battery in overcharging. Preferred examples of the aromatic compound include cyclohexylbenzene, fluorocyclohexylbenzene compound (1-fluoro-2-cyclohexylbenzene, 1-fluoro-3-cyclohexylbenzene, 1-fluoro-4-cyclohexylbenzene), tert-butylbenzene, tert-amylbenzene, 1-fluoro-4-tert-butylbenzene, 1,3-di-tert-butylbenzene, biphenyl, terphenyl (o-, m-, p-form), diphenyl ether, fluorobenzene, difluorobenzene (o-, m-, p-form), 2,4-difluoroanisole, partially hydrogenated terphenyl (1,2-dicyclohexylbenzene, 2-phenylbicyclohexyl, 1,2-diphenylcyclohexane, o-cyclohexylbiphenyl), etc. One or more of these compounds may be used herein either singly or as combined.

[Production of Nonaqueous Electrolytic Solution]

The nonaqueous electrolytic solution of the present invention can be produced, for example, by mixing the above-mentioned nonaqueous solvents followed by dissolving therein the above-mentioned electrolyte salt and at least one compound selected from the above general formulae (I) and (II) in an amount of from 0.01 to 10% by mass of the resulting nonaqueous electrolytic solution.

In this case, the nonaqueous solvent to be used, and the compound to be added to the nonaqueous electrolytic solution are preferably previously purified within a range not significantly detracting from the producibility, in which, therefore, the impurity content is preferably as low as possible.

The nonaqueous electrolytic solution of the present invention is favorably used for the electrolytic solution for lithium primary batteries and lithium secondary batteries. Further, the nonaqueous electrolytic solution of the present invention is also usable as an electrolytic solution for electric double layer capacitors or as an electrolytic solution for hybrid capacitors. Of those, the nonaqueous electrolytic solution of the present invention is most favorable for lithium secondary batteries.

[Lithium Battery]

The lithium battery of the present invention collectively includes a lithium primary battery and a lithium secondary battery, comprising a positive electrode, a negative electrode and the above-mentioned nonaqueous electrolytic solution of an electrolyte salt dissolved in a nonaqueous solvent, and is characterized in that a hydroxy acid derivative compound represented by the above-mentioned general formula (I) or (II) is in the nonaqueous electrolytic solution in an amount of from 0.01 to 10% by mass of the nonaqueous electrolytic solution.

In the lithium battery of the present invention, the other constitutive components such as a positive electrode and a negative electrode except for the nonaqueous electrolytic solution can be used with no limitation.

For example, as the positive electrode active material for lithium secondary battery, usable are complex metal oxides of lithium containing any of cobalt, manganese or nickel. One or more such positive electrode active materials may be used either singly or as combined.

The complex metal oxides include, for example, $LiCoO_2$, $LiMn_2O_4$, $LiNiO_2$, $LiCO_{1-x}Ni_xO_2$ ($0.01<x<1$), $LiCO_{1/3}Ni_{1/3}Mn_{1/3}O_2$, $LiNi_{1/2}Mn_{3/2}O_4$, $LiCo_{0.98}Mg_{0.02}O_2$, etc. Combinations of $LiCoO_2$ and $LiMn_2O_4$; $LiCoO_2$ and $LiNiO_2$; $LiMn_2O_4$ and $LiNiO_2$ are acceptable herein.

For enhancing the safety in overcharging or enhancing the cycle property, the lithium complex oxide may be partly substituted with any other element for enabling the use of the battery at a charging potential of 4.3 V or more. For example, a part of cobalt, manganese and nickel may be substituted with at least one element of Sn, Mg, Fe, Ti, Al, Zr, Cr, V, Ga, Zn, Cu, Bi, Mo, La, etc.; or O may be partly substituted with S or F; or the oxide may be coated with a compound containing such other element.

Of those, preferred are lithium complex metal oxides such as $LiCoO_2$, $LiMn_2O_4$ and $LiNiO_2$, with which the positive electrode charging potential in a full-charging state may be 4.3 V or more, based on Li. More preferred are lithium complex oxides usable at 4.4 V or more, such as $LiCo_{1-x}M_xO_2$ (where M is at least one element of Sn, Mg, Fe, Ti, Al, Zr, Cr, V, Ga, Zn and Cu; $0.001 \leq x \leq 0.05$), $LiCO_{1/3}Ni_{1/3}Mn_{1/3}O_2$, and $LiNi_{1/2}Mn_{3/2}O_4$.

Further, lithium-containing olivine-type phosphates are also usable as the positive electrode active material. Their concrete examples include $LiFePO_4$, $LiCoPO_4$, $LiNiPO_4$, $LiMnPO_4$, etc.

The lithium-containing olivine-type phosphates may be partly substituted with any other element. For example, apart of iron, cobalt, nickel and manganese therein may be substituted with at least one element selected from Co, Mn, Ni, Mg, Al, B, Ti, V, Nb, Cu, Zn, Mo, Ca, Sr, W and Zr; or the phosphates may be coated with a compound containing any of these other elements or with a carbon material. Of those, preferred are $LiFePO_4$ and $LiMnPO_4$.

The lithium-containing olivine-type phosphate may be combined with, for example, the above-mentioned positive electrode active material.

Not specifically defined, the electroconductive agent of the positive electrode may be any electron-transmitting material not undergoing chemical change. For example, it includes graphites such as natural graphite (flaky graphite, etc.), artificial graphite, etc.; carbon blacks such as acetylene black, Ketjen black, channel black, furnace black, lamp black, thermal black, etc. Graphites and carbon blacks may be combined suitably. The amount of the electroconductive agent to be added to the positive electrode mixture is preferably from 1 to 10% by mass, more preferably from 2 to 5% by mass.

The positive electrode may be formed by mixing the above-mentioned positive electrode active material with an electroconductive agent such as acetylene black, carbon black or the like, and with a binder such as polytetrafluoroethylene (PTFE), polyvinylidene fluoride (PVDF), styrene/butadiene copolymer (SBR), acrylonitrile/butadiene copolymer (NBR), carboxymethyl cellulose (CMC), ethylene/propylene/diene terpolymer or the like, then adding thereto a high-boiling-point solvent such as 1-methyl-2-pyrrolidone or the like, and kneading them to give a positive electrode mixture, thereafter applying the positive electrode mixture onto an aluminium foil or a stainless lath plate or the like serving as a collector, and drying and shaping it under pressure, and then heat-treating it in vacuum at a temperature of from 50° C. to 250° C. or so for about 2 hours.

The density of the part except the collector of the positive electrode may be generally at least 1.5 g/cm³, and for further increasing the capacity of the battery, the density is preferably at least 2 g/cm³, more preferably at least 3 g/cm³, even more preferably at least 3.6 g/cm³.

For the positive electrode for lithium primary battery, there are mentioned oxides or chalcogen compounds of one or more metal elements such as $CuO$, $Cu_2O$, $Ag_2O$, $Ag_2CrO_4$, $CuS$, $CuSO_4$, $TiO_2$, $TiS_2$, $SiO_2$, $SnO$, $V_2O_5$, $V_6O_{12}$, $VO_x$, $Nb_2O_5$, $Bi_2O_3$, $Bi_2Pb_2O_5$, $Sb_2O_3$, $CrO_3$, $Cr_2O_3$, $MoO_3$, $WO_3$, $SeO_2$, $MnO_2$, $Mn_2O_3$, $Fe_2O_3$, $FeO$, $Fe_3O_4$, $Ni_2O_3$, $NiO$, $CoO_3$, $CoO$, etc.; sulfur compounds such as $SO_2$, $SOCl_2$, etc.; carbon fluorides (fluorographite) represented by a general formula $(CF_x)_n$, etc. Above all, preferred are $MnO_2$, $V_2O_5$, fluorographite, etc.

As the negative electrode active material for lithium secondary battery, usable are one or more of lithium metal, lithium alloys, carbon materials [graphites such as artificial graphite, natural graphite, etc.;], tin, tin compounds, silicon, silicon compounds and the like capable of absorbing and releasing lithium, either singly or as combined.

Of those, preferred are high-crystalline carbon materials such as artificial graphite, natural graphite or the like of which the ability of absorbing and releasing lithium ions is good. More preferred is a carbon material having a graphite-type crystal structure where the lattice (002) spacing ($d_{002}$) is at most 0.340 nm (nanometers), especially from 0.335 to 0.337 nm. More preferably, the high-crystalline carbon material is coated with a low-crystalline carbon material, as capable of improving the low-temperature cycle property. When such a high-crystalline carbon material is used, then it may react with a nonaqueous electrolytic solution in charging thereby worsening the low-temperature and high-temperature cycle property; however, in the lithium secondary battery of the present invention, the reaction with the nonaqueous electrolytic solution can be retarded.

The metal compound capable of absorbing and releasing lithium, serving as a negative electrode active material, includes compounds containing at least one metal element of Si, Ge, Sn, Pb, P, Sb, Bi, Al, Ga, In, Ti, Mn, Fe, Co, Ni, Cu, Zn, Ag, Mg, Sr, Ba, etc. These metal compounds may have any morphology of simple substances, alloys, oxides, nitrides, sulfides, borides, alloys with lithium or the like; but preferred are any of simple substances, alloys, oxides and alloys with lithium, as capable of increasing the battery capacity. Above all, more preferred are those containing at least one element selected from Si, Ge and Sn, and even more preferred are those containing at least one element selected from Si and Sn, as capable of increasing the capacity of the battery.

The negative electrode may be formed, using the same electroconductive agent, binder and high-boiling point solvent as in the formation represented by the above-mentioned positive electrode. These are mixed and kneaded to give a negative electrode mixture, then the negative electrode mixture is applied onto a copper foil or the like serving as a collector, then dried and shaped under pressure, and thereafter heat-treated in vacuum at a temperature of from 50° C. to 250° C. or so for about 2 hours.

In case where graphite is used as the negative electrode active material, the density of the part except the collector of the negative electrode may be generally at least 1.4 g/cm$^3$, and for further increasing the capacity of the battery, the density is preferably at least 1.6 g/cm$^3$, more preferably at least 1.7 g/cm$^3$.

As the negative electrode active material for lithium primary battery, usable is a lithium metal or a lithium alloy.

As the separator for battery, usable is a single-layer or laminate porous film of polyolefin such as polypropylene, polyethylene or the like, as well as a woven fabric, a non-woven fabric, etc.

The structure of the lithium secondary battery is not specifically defined. The battery may be a coin-shaped battery, a cylindrical battery, a square-shaped battery, or a laminate-type battery, each having a single-layered or multi-layered separator.

The lithium secondary battery of the present invention exhibits excellent long-term cycle property even when the final charging voltage is 4.2 V or higher and particularly 4.3 V or higher. Furthermore, the cycle property is good even when the final charging voltage is 4.4 V. The final discharging voltage can be 2.5 V or more and further 2.8 V or more. The current value is not specifically defined. In general, the current mode is a constant current discharging mode within a range of from 0.1 to 3 C. The lithium secondary battery of the present invention may be charged and discharged at −40° C. to 100° C. and preferably at 0° C. to 80° C.

In the present invention, as a countermeasure against the increase in the internal pressure of the lithium secondary battery, there may be employed a method of providing a safety valve in the battery cap or a method of forming a cutout in the battery component such as the battery can, the gasket or the like. In addition, as a safety countermeasure against overcharging, a current breaker capable of detecting the internal pressure of the battery to cut off the current may be provided in the battery cap.

[Hydroxy Acid Derivative Compound]

The novel compound of the present invention, hydroxy acid derivative compound is represented by the following general formula (III) or (IV):

[Formula 4]

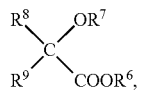   (III)

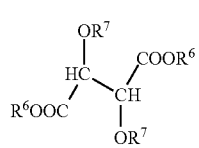   (IV)

(In the general formulae (III) and (IV), R$^6$ represents a linear or branched alkenyl group having from 2 to 6 carbon atoms, or a linear or branched alkynyl group having from 3 to 6 carbon atoms; R$^7$ represents a sulfonyl group (—SO$_2$R$^{10}$) (where R$^{10}$ represents a linear or branched alkyl group having from 1 to 6 carbon atoms, or a linear or branched alkyl group having from 1 to 6 carbon atoms in which at least one hydrogen atom is substituted with a halogen atom), or a formyl group (—CHO); R$^8$ and R$^9$ each represent a hydrogen atom or a methyl group; provided that, in the general formula (III), when R$^7$ is a sulfonyl group (—SO$_2$R$^{10}$), then R$^6$ is a linear or branched alkenyl group having from 2 to 6 carbon atoms.)

In the general formula (III) and (IV), the linear or branched alkenyl group having from 2 to 6 carbon atoms, or the linear or branched alkynyl group having from 3 to 6 carbon atoms for the substituent R$^6$ is the same as those in the general formulae (I) and (II) described above, and this is omitted in this section for preventing overlapping. In this case, the substituent R$^1$ in the general formulae (I) and (II) is read as the substituent R$^6$ in the general formulae (III) and (IV).

Similarly, the substituents R$^2$, R$^3$, R$^4$ and R$^5$ in the general formulae (I) and (II) are read as the substituents R$^7$, R$^8$, R$^9$ and R$^{10}$ in the general formulae (III) and (IV).

Typical examples of the hydroxy acid derivative compound of the present invention include formyloxycarboxylate compounds, alkylsulofnyloxycarboxylate compounds, etc.

(Formyloxycarboxylate Compound)

The formyloxycarboxylate compound may be produced according to the following methods (a) to (c), to which, however, the present invention is not limited.

(a) A method of condensing a hydroxycarboxylate with formic acid in the presence or absence of a solvent, in the absence of a catalyst or in the presence of an acid catalyst, and in the presence or absence of a dehydrating agent (hereinafter this may be referred to as "method (a)").

(b) A method of interesterifying a hydroxycarboxylate with a formate in the presence or absence of a solvent, and in the presence of an acid catalyst (hereinafter this may be referred to as "method (b)").

(c) A method of esterifying a hydroxycarboxylate with a mixed anhydride or a mixture of a carboxylic acid anhydride and formic acid in the presence or absence of a solvent (hereinafter this may be referred to as "method (c)").

[Method (a)]

The method (a) is a method of condensing a hydroxycarboxylate with formic acid in the presence or absence of a solvent, in the absence of a catalyst or in the presence of an acid catalyst, and in the presence or absence of a dehydrating agent.

In the method (a), the amount of formic acid to be used is preferably from 1 to 20 mols relative to 1 mol of the hydroxycarboxylate, more preferably from 1 to 10 mols, even more preferably from 1 to 5 mols.

Not specifically defined, the solvent to be used in the method (a) may be any one inert to the reaction. For example, it includes aliphatic hydrocarbons such as hexane, heptane, cyclohexane, etc.; halogenohydrocarbons such as dichloroethane, dichloropropane, etc.; aromatic hydrocarbons such as toluene, xylene, etc.; halogenoaromatichydrocarbons such as chlorobenzene, fluorobenzene, etc.; ethers such as diethyl ether, diisopropyl ether, dioxane, dimethoxyethane, diethoxyethane, diglyme, triglyme, etc.; nitriles such as acetonitrile, propionitrile, etc.; sulfoxides such as dimethyl sulfoxide, etc.; nitro compounds such as nitromethane, nitroethane, etc.; and their mixtures. Of those, preferred are aliphatic or aromatic hydrocarbons having from 6 to 9 carbon atoms such as hexane, heptane, toluene or the like hardly miscible with water.

The amount of the solvent to be used is preferably from 0 to 30 parts by mass relative to one part by mass of the hydroxycarboxylate, more preferably from 1 to 10 parts by mass.

In the method (a), formic acid exists, and therefore the reaction may go on in the absence of a catalyst; however, when an acid catalyst is used, then the reaction may be promoted. The usable acid catalyst includes mineral acids such as sulfuric acid, phosphoric acid, etc.; organic acids such as paratoluenesulfonic acid, methanesulfonic acid, trifluoromethanesulfonic acid, etc.; Lewis acids with trifluoroboron, tetra-iso-propoxytitanium or a rare earth metal; solid acids such as zeolite, acidic resins, etc.; and their mixtures.

The amount of the catalyst to be used is preferably from 0.001 to 5 mols relative to 1 mol of the hydroxycarboxylate, more preferably from 0.01 to 1 mol, even more preferably from 0.01 to 0.5 mols, from the viewpoint of inhibiting side products.

As a method of reducing the amount of formic to be used relative to the hydroxycarboxylate for efficient ester production, a dehydrating agent may be used. The dehydrating agent includes at least one selected from dicyclohexylcarbodiimide, N,N'-carbonyldiimidazole, di-2-pyridyl carbonate, phenyl dichlorophosphate, a mixture of ethyl diethylazodicarboxylate and triphenyl phosphine, etc. The amount of the dehydrating agent to be used is preferably from 0.9 to 10 mols relative to 1 mol of the hydroxycarboxylate, more preferably from 1 to 5 mols and further preferably from 1 to 2 mols.

In the reaction of the method (a), the lower limit of the reaction temperature in the case where a dehydrating agent is not used is preferably 0° C. or higher, more preferably 20° C. or higher from the viewpoint of not lowering the reactivity. From the viewpoint of inhibiting side reaction and decomposition of formic acid and the product, the upper limit of the reaction temperature is preferably 200° C. or lower, more preferably 150° C. or lower.

The lower limit of the reaction temperature in the case where a dehydrating agent is used is preferably −20° C. or higher, and more preferably 0° C. or higher from the viewpoint of not lowering the reactivity. From the viewpoint of inhibiting side reaction and decomposition of formic acid and the product, the upper limit of the reaction temperature is preferably 100° C. or lower, more preferably 50° C. or lower.

The reaction time for the method (a) may suitably vary depending on the reaction temperature and the scale; however, when the reaction time is too short, unreacted compounds may remain, but on the contrary, when the reaction time is too long, the product may decompose and side reaction may occur. Therefore, preferably, the reaction time is from 0.1 to 12 hours, more preferably from 0.2 to 6 hours. The reaction pressure may be within a range of from 0.1 to 10 atmosphere, preferably from 0.5 to 5 atmospheres.

[Method (b)]

The method (b) is a method of interesterifying a hydroxycarboxylate with a formate in the presence or absence of a solvent and in the presence of an acid catalyst.

In the method (b), the amount of the formate to be used is preferably from 1 to 20 mols relative to 1 mol of the hydroxycarboxylate, more preferably from 1 to 10 mols, even more preferably from 1 to 5 mols.

The formate to be used in the method (b) includes at least one selected from formates such as methyl formate, ethyl formate, propyl formate, butyl formate, etc.

In the method (b), the formate may serve also as a solvent, and therefore the reaction may go on in the absence of a solvent; however, a solvent inert to the reaction may be used. The usable solvent includes aliphatic hydrocarbons, halo genohydrocarbons, aromatic hydrocarbons, halogenoaromatic hydrocarbons, ethers, nitriles, sulfoxides, nitro compounds such as those described for the method (a); and in addition, ketones such as 3-pentanone, cyclohexanone, etc.; amides such as N,N-dimethylformamide; and their mixtures.

The amount of the solvent to be used is preferably from 0 to 10 parts by mass relative to 1 part by mass of the hydroxycarboxylate, more preferably from 0 to 5 parts by mass.

The catalyst to be used in the method (b) includes acids, bases and others; but preferred is use of an acid catalyst by which the side product, formic acid may be neutralized and deactivated. The usable acid catalyst includes mineral acids, organic acids, Lewis acids, solid acids such as zeolite, acidic resins and the like, and their mixtures, like those described for the method (a). The usable base includes metal alcoholates such as sodium methylate, sodium ethylate, potassium tert-butoxide, etc.; metal hydrides such as sodium hydride, potassium hydride, etc.; alkali metals such as sodium, potassium, lithium, etc.; and their mixtures.

The amount of the catalyst to be used is preferably from 0.001 to 5 mols relative to 1 mol of the hydroxycarboxylate from the viewpoint of inhibiting side products, more preferably from 0.01 to 1 mol, even more preferably from 0.01 to 0.3 mols.

In the reaction of the method (b), the lower limit of the reaction temperature is preferably 0° C. or higher, more preferably 20° C. or higher from the viewpoint of not lowering the reactivity. From the viewpoint of inhibiting side reaction and decomposition of the product, the upper limit of the reaction temperature is preferably 250° C. or lower, more preferably 150° C. or lower.

The reaction time may suitably vary depending on the reaction temperature and the scale; however, when the reaction time is too short, unreacted compounds may remain, but on the contrary, when the reaction time is too long, the product may decompose and side reaction may occur. Therefore, preferably, the reaction time is from 0.1 to 12 hours, more preferably from 0.2 to 6 hours. The reaction pressure may be within a range of from 0.1 to 10 atmosphere, preferably from 0.5 to 5 atmospheres.

[Method (c)]

The method (c) is a method for esterifying a hydroxycarboxylate with a mixed anhydride, or a mixture of a carboxylic acid anhydride and formic acid, in the presence or absence of a solvent.

The carboxylic acid anhydride is preferably one having a total carbon number of from 3 to 10; however, in the method (c), formic anhydride is unstable and could not be used alone, and therefore, a mixed anhydride of formic acid and acetic acid, or a mixture of acetic anhydride and formic acid may be used.

In the reaction of the method (c), the amount to be used of the mixed anhydride of formic acid and acetic acid, or the formic acid to be a mixture with acetic anhydride to be reacted with the hydroxycarboxylate is preferably from 0.9 to 10 mols relative to 1 mol of the hydroxycarboxylate, more preferably from 1 to 3 mols, even more preferably from 1 to 1.5 mols.

The solvent usable in the method (c) is not specifically defined, and may be any one inert to the reaction. The usable solvent includes aliphatic hydrocarbons, halo genohydrocarbons, aromatic hydrocarbons, halogenoaromatic hydrocarbons, ethers, nitriles, sulfoxides, nitro compounds such as those described for the method (a); and in addition, ketones such as 3-pentanone, cyclohexanone, etc.; amides such as N,N-dimethylformamide; and their mixtures.

The amount of the solvent to be used is preferably from 0 to 30 parts by mass relative to 1 part by mass of the hydroxycarboxylate, more preferably from 1 to 15 parts by mass.

In the reaction of the method (c), preferably a base exists as promoting the reaction. The base may be any of an inorganic base or an organic base.

The inorganic base includes potassium carbonate, sodium carbonate, calcium hydroxide, calcium oxide, etc.

The organic base includes linear or branched aliphatic tertiary amines, mono- or poly-substituted pyrroles, pyrrolidones, imidazoles, imidazolidinones, pyridines, pyrimidines, quinolines, N,N-dialkylcarboxyamides, etc. Of those, more preferred are trialkylamines such as trimethylamine, triethylamine, tripropylamine, tributylamine, ethyldiisopropylamine, etc.; and pyridine, N-methylpyrrolidone, N,N-dimethylacetamide, N,N-dimethylaminopyridine, and 1,3-dimethylimidazolidinone. One or more these bases may be used here either singly or as combined.

The amount of the base to be used is preferably from 0.8 to 5 mols relative to 1 mol of the hydroxycarboxylate from the viewpoint of inhibiting side products, more preferably from 1 to 3 mols, even more preferably from 1 to 1.5 mols.

In the reaction of the method (c), the lower limit of the reaction temperature is preferably −20° C. or higher from the viewpoint of not lowering the reactivity, more preferably −10° C. or higher. From the viewpoint of inhibiting side reaction and decomposition of the product, the upper limit of the reaction temperature is preferably 80° C. or lower, more preferably 60° C. or lower.

The reaction time may suitably vary depending on the reaction temperature and the scale; however, when the reaction time is too short, unreacted compounds may remain, but on the contrary, when the reaction time is too long, the product may decompose and side reaction may occur. Therefore, preferably, the reaction time is from 0.1 to 12 hours, more preferably from 0.2 to 6 hours.

(Alkylsulfonyloxycarboxylate Compound)

The method for producing the alkylsulfonyloxycarboxylate compound is not specifically defined. For example, it may be produced by reacting a hydroxycarboxylate and an alkanesulfonyl halide or an alkanesulfonic acid anhydride in the presence or absence of a solvent and in the presence of a base for esterification (hereinafter this may be referred to as "method (d)").

The starting material, hydroxycarboxylate may be produced according to an already-existing general method. To it, for example, applicable is the method described in Advanced Organic Chemistry, 4th Ed., Jerry March, John Wiley & Sons, pp. 393-400.

The amount of the alkanesulfonyl halide or the alkanesulfonic acid anhydride to be used in the method (d) is preferably from 0.9 to 10 mols per 1 mol of the hydroxycarboxylate, more preferably from 1 to 3 mols, even more preferably from 1 to 1.5 mols.

The usable alkanesulfonyl halide includes methanesulfonyl chloride, ethanesulfonyl chloride, trifluoromethanesulfonyl chloride, methanesulfonyl bromide, ethanesulfonyl bromide, trifluoromethanesulfonyl bromide, etc.

Of those, preferred are sulfonyl chlorides such as methanesulfonyl chloride, ethanesulfonyl chloride, trifluoromethanesulfonyl chloride and the like that are industrially inexpensive.

The usable alkanesulfonic acid anhydride includes methanesulfonic acid anhydride, ethanesulfonic acid anhydride, trifluoromethanesulfonic anhydride, etc.

The solvent is not specifically defined and may be any one inert to the reaction. The usable solvent includes aliphatic hydrocarbons, halogenohydrocarbons, aromatic hydrocarbons, halogenoaromatic hydrocarbons, ethers, nitriles, sulfoxides, nitro compounds such as those described for the method (a); and in addition, amides such as N,N-dimethylformamide; esters such as ethyl acetate, dimethyl carbonate, etc.; and their mixtures. Of those, especially preferred are aromatic hydrocarbons such as toluene, xylene, etc.

The amount of the solvent to be used is preferably from 0 to 30 parts by mass relative to 1 part by mass of the hydroxycarboxylate, more preferably from 1 to 15 parts by mass.

The base may be any of an inorganic base or an organic base. The usable base includes inorganic bases and organic bases such as those described for the method (c).

The amount of the base to be used is preferably from 0.8 to 5 mols relative to 1 mol of the hydroxycarboxylate from the viewpoint of inhibiting side products, more preferably from 1 to 3 mols, even more preferably from 1 to 1.5 mols.

In the reaction of the method (d), the lower limit of the reaction temperature is preferably −20° C. or higher, more preferably −10° C. or higher from the viewpoint of not lowering the reactivity. From the viewpoint of inhibiting side reaction and decomposition of the product, the upper limit of the reaction temperature is preferably 80° C. or lower, more preferably 60° C. or lower.

The reaction time may suitably vary depending on the reaction temperature and the scale; however, when the reaction time is too short, unreacted compounds may remain, but on the contrary, when the reaction time is too long, the product may decompose and side reaction may occur. Therefore, preferably, the reaction time is from 0.1 to 12 hours, more preferably from 0.2 to 6 hours.

EXAMPLES

Production Examples for the hydroxy acid derivative compound of the present invention, and Examples of an electrolytic solution using it are shown below; however, the present invention should not be restricted by these Examples.

Production Example 1

Production of 2-propenyl 2-(methanesulfonyloxy)propionate 32.00 g (246 mmol) of 2-propenyl 2-hydroxypropionate and 31.3 g (310 mmol) of triethylamine were dissolved in 150 g of toluene (solvent), and 35.6 g (310 mmol) of methanesulfonyl chloride was dropwise added thereto at 10° C., taking 20 minutes. These were reacted at room temperature for 1 hour, the reaction liquid was washed twice with water, then the organic layer was separated and concentrated. The concentrate was purified through silica gel column chromatography, and from the fraction taken with hexane/ethyl acetate=5/1, 27 g (yield 53%) of 2-propenyl 2-(methanesulfonyloxy)propionate was obtained.

The obtained 2-propenyl 2-(methanesulfonyloxy)propionate was analyzed for $^1$H-NMR, $^{13}$C-NMR and mass spectrometry to confirm its structure. The results are shown below.

(1) $^1$H-NMR (300 MHz, CDCl$_3$): δ=5.92 (ddt, J=17.2, 10.5, 5.6 Hz, 1H), 5.36 (ddd, J=17.2, 1.5, 1.2 Hz, 1H), 5.31 (ddd, J=10.5, 1.5, 1.2 Hz, 1H), 4.69 (qd, J=7.1, 1.2 Hz, 2H), 3.15 (s, 3H), 1.63 (d, J=7.1 Hz, 3H).

(2) $^{13}$C-NMR (75 MHz, CDCl$_3$): δ=169.2, 131.1, 119.4, 74.2, 66.4, 39.2, 18.4.

(3) Mass Spectrometry: MS(CI) [M+1]=209.

Production Example 2

Production of 2-propenyl 2-(formyloxy)propionate 5.00 g (41 mmol) of 2-propenyl 2-hydroxypropionate, 2.48 g (54 mmol) of formic acid, and 1.00 g (8 mmol) of 4,4-dimethylaminopyridine (nucleating agent) were dissolved in 30 g of 1,2-dichloroethane (solvent), and a mixed solution of 12.00 g (171 mmol) of N,N'-dicyclohexylcarbodiimide (dehydrating agent) and 20 g of 1,2-dichloroethane (solvent) was added thereto at 10° C., taking 30 minutes. These were reacted at room temperature for 3 hours, the reaction liquid was filtered to remove N,N'-dicyclohexylurea, and the filtrate was concentrated. The concentrate was purified through silica gel column chromatography, and from the fraction taken with hexane/ethyl acetate=8/1, 3.5 g (yield 54%) of 2-propenyl 2-(formyloxy)propionate was obtained.

The obtained 2-propenyl 2-(formyloxy)propionate was analyzed for $^1$H-NMR, $^{13}$C-NMR and mass spectrometry to confirm its structure. The results are shown below.

(1) $^1$H-NMR (300 MHz, CDCl$_3$): δ=8.10 (q, J=0.5 Hz, 1H), 5.91 (ddt, J=17.3, 10.5, 5.9 Hz, 1H), 5.35 (ddd, J=17.3, 1.2, 1.5 Hz, 2H), 5.27 (ddd, 10.5, 1.5 Hz, 1.2 Hz, 1H), 5.25 (dq, J=7.1, 1.0 Hz, 1H), 4.67 (dt, J=1.5, 5.6 Hz, 1H), 1.55 (d, J=7.1 Hz, 3H).

(2) $^{13}$C-NMR (75 MHz, CDCl$_3$): δ=169.8, 160.0, 131.4, 118.9, 68.1, 66.0, 17.0.

(3) Mass Spectrometry: MS(CI) [M+1]=159.

Production Example 3

Production of 2-propynyl 2-(formyloxy)propionate 40.00 g (444 mmol) of 2-hydroxypropionate and 1.0 mL of sulfuric acid were dissolved in 35 mL of toluene, and 74.68 g (1.332 mmol) of propargyl alcohol was added thereto, and using a Dean-Stark device under normal pressure, the side-product water (7.99 g) was removed, and the reaction was further continued under reflux under normal pressure. After 3 hours, the reaction liquid was analyzed through thin-layer chromatography in which the absence of the starting materials was confirmed, and then the reaction liquid was neutralized with sodium acetate added thereto, filtered, and the filtrate was concentrated. The residue was purified through reduced-pressure distillation to give 19.96 g (yield 35%) of 2-propynyl 2-hydroxypropionate [namely, propargyl 2-hydroxypropionate].

19.96 g (156 mmol) of the obtained 2-propynyl 2-hydroxypropionate, 7.17 g (156 mmol) of formic acid, and 15.23 g (125 mmol) of 4,4-dimethylaminopyridine (nucleating agent) were dissolved in 100 g of 1,2-dichloroethane (solvent), and a mixed solution of 35.35 g (171 mmol) of N,N'-dicyclohexylcarbodiimide (dehydrating agent) and 50 g of 1,2-dichloroethane was added thereto at 10° C., taking 30 minutes. These were reacted at room temperature for 4 hours, and the absence of the starting materials was confirmed through gas chromatography. Subsequently, the reaction liquid was filtered to remove N,N'-dicyclohexylurea, and the filtrate was concentrated. The concentrate was purified through silica gel column chromatography, and from the fraction taken with hexane/ethyl acetate=4/1, 20.78 g (yield 85%) of 2-propynyl 2-(formyloxy)propionate was obtained.

The obtained 2-propynyl 2-(formyloxy)propionate was analyzed for $^1$H-NMR, $^{13}$C-NMR and mass spectrometry to confirm its structure. The results are shown below.

(1) $^1$H-NMR (300 MHz, CDCl$_3$): δ=8.09 (s, 1H), 5.27 (q, J=7.0 Hz, 1H), 4.77-4.75 (m, 2H), 2.54 (t, J=2.6 Hz, 1H), 1.57 (d, J=7.0 Hz, 3H).

(2) $^{13}$C-NMR (75 MHz, CDCl$_3$): δ=169.3, 159.8, 76.8, 75.6, 67.8, 52.9, 16.7.

(3) Mass Spectrometry: MS(CI) [M+1]=171.

Examples 1 to 4

(1) Preparation of Nonaqueous Electrolytic Solution

LiPF$_6$ to be 1 M was dissolved in a nonaqueous solvent of EC/MEC/DEC=30/35/35 (ratio by volume), and further methyl 2-(methanesulfonyloxy)propionate [namely, methyl 2-(methylsulfonyloxy)propionate] was added thereto to prepare a nonaqueous electrolytic solution, in an amount of 0.1% by mass of the resulting nonaqueous electrolytic solution (Example 1), 1% by mass (Example 2), 5% by mass (Example 3) and 10% by mass (Example 4).

(2) Production of Lithium Ion Secondary Battery

93% by mass of LiCoO$_2$ (positive electrode active material) and 3% by mass of acetylene black (electroconductive agent) were mixed, and added to and mixed with a solution previously prepared by dissolving 4% by mass of polyvinylidene fluoride (binder) in 1-methyl-2-pyrrolidone, thereby preparing a positive electrode mixture paste. The positive electrode mixture paste was applied onto both surfaces of an aluminium foil (collector), dried, processed under pressure and cut into a predetermined size, thereby producing a long rectangular, positive electrode sheet. The density of apart of the positive electrode except the collector was 3.6 g/cm$^3$. 95% by mass of artificial graphite (d$_{002}$=0.335 nm, negative electrode active material) was added to and mixed with a solution previously prepared by dissolving 5% by mass of polyvinylidene fluoride (binder) in 1-methyl-2-pyrrolidone, thereby preparing a negative electrode mixture paste. The negative electrode mixture paste was applied onto both surfaces of a copper foil (collector), dried, processed under pressure and cut into a predetermined size, thereby producing a long rectangular, negative electrode sheet. The density of a part of the negative electrode except the collector was 1.7 g/cm$^3$. The positive electrode sheet, a porous polyethylene film separator, the negative electrode sheet and a separator were laminated in that order, and the resulting laminate was coiled up. The coil was housed into a nickel-plated, iron-made cylindrical battery can serving also as a negative electrode terminal. Further, the nonaqueous electrolytic solution was injected thereinto, and the can was calked with a battery cap having a positive electrode terminal, via a gasket therebetween, thereby constructing a 18650-type cylindrical battery. The positive electrode terminal was connected to the positive electrode sheet via an aluminium lead tab therebetween; and the negative electrode can was previously connected to the negative electrode sheet inside the battery, via a nickel lead tab therebetween.

(3) Evaluation of Low-Temperature Cycle Property

In a thermostat chamber kept at 25° C., the battery constructed as in the above was charged up to 4.2 V (charging final voltage) with a constant current of 1 C, then charged for 2.5 hours at the constant voltage of 4.2 V, and thereafter this was discharged under a constant current of 1 C to a discharge voltage of 3.0 V (discharging final voltage). Next, in a thermostat chamber kept at 0° C., this was charged up to 4.2 V with a constant current of 1 C, then charged for 2.5 hours at the constant voltage of 4.2 V, and thereafter this was discharged under a constant current of 1 C to a discharge voltage of 3.0 V. The cycle of charging and discharging was repeated 50 times. After 50 cycles at 0° C., the discharge capacity retention rate (%) of the battery was determined according to the following formula. The results are shown in Table 1.

Discharge Capacity Retention Rate (%) after 50 cycles at 0° C.=(discharge capacity in 50 cycles at 0° C./discharge capacity in 1 cycle at 0° C.)×100.

(4) Evaluation of High-Temperature Cycle Property

In a thermostat chamber kept at 60° C., the battery constructed as in the above was charged up to 4.2 V (charging final voltage) with a constant current of 1 C, then charged for 2.5 hours at the constant voltage of 4.2 V, and thereafter this was discharged under a constant current of 1 C to a discharge voltage of 3.0 V (discharging final voltage). The cycle of charging and discharging was repeated 100 times. After 100 cycles at 60° C., the discharge capacity retention rate (%) of the battery was determined according to the following formula. The results are shown in Table 1.

Discharge Capacity Retention Rate (%) after 100 cycles at 60° C.=(discharge capacity in 100 cycles at 60° C./discharge capacity in 1 cycle at 60° C.)×100.

Examples 5 to 15

Cylindrical batteries were produced in the same manner as in Example 1, for which, however, the nonaqueous electrolytic solution was prepared by adding thereto, in place of methyl 2-(methanesulfonyloxy)propionate, 1% by mass, relative to the resulting nonaqueous electrolytic solution, of methyl 2-(formyloxy)propionate (Example 5), 1% by mass of 2-propenyl 2-(methanesulfonyloxy)propionate (obtained in Production Example 1) (Example 6), 1% by mass of 2-propenyl 2-(formyloxy)propionate (obtained in Production Example 2) (Example 7), 1% by mass of 2-propynyl 2-(methanesulfonyloxy)propionate (Example 8), 1% by mass of 2-propynyl 2-(formyloxy)propionate (obtained in Production Example 3) (Example 9), 1% by mass of methyl methanesulfonyloxyacetate (Example 10), 1% by mass of methyl formyloxyacetate (Example 11), 1% by mass of methyl 2-(methanesulfonyloxy)-2-methylpropionate (Example 12), 1% by mass of methyl 2-(formyloxy)-2-methylpropionate (Example 13), 1% by mass of dimethyl 2,3-di(methanesulfonyloxy)succinate (Example 14), or 1% by mass of dimethyl 2,3-di(formyloxy)succinate (Example 15); and the batteries were evaluated. The results are shown in Table 1.

Example 16

A cylindrical battery was produced in the same manner as in Example 1, for which, however, LiPF$_6$ to be 0.95 M and LiN(SO$_2$CF$_3$)$_2$ to be 0.05 M were dissolved in a nonaqueous solvent of EC/VC/MEC/DEC=23/2/50/25 (ratio by volume), and further, 1% by mass of methyl 2-(methanesulfonyloxy) propionate and 1% by mass of 1,3-propanesultone, relative to the resulting nonaqueous electrolytic solution, were added thereto to prepare a nonaqueous electrolytic solution, and the battery was evaluated. The result is shown in Table 1.

Example 17

A cylindrical battery was produced in the same manner as in Example 1, for which, however, LiPF$_6$ to be 0.95 M and LiBF$_4$ to be 0.05 M were dissolved in a nonaqueous solvent of FEC/PC/MEC/DMC=20/5/50/25 (ratio by volume), and further, 1% by mass of methyl 2-(methanesulfonyloxy)propionate, relative to the resulting nonaqueous electrolytic solution, was added thereto to prepare a nonaqueous electrolytic solution, and the battery was evaluated. The result is shown in Table 1.

Comparative Example 1

A cylindrical battery was produced in the same manner as in Example 1, for which, however, methyl 2-(methanesulfonyloxy)propionate was not added to the nonaqueous electrolytic solution, and the battery was evaluated. The result is shown in Table 1.

Comparative Example 2

A cylindrical battery was produced in the same manner as in Example 1, for which, however, 1% by mass, relative to the resulting nonaqueous electrolytic solution, of dimethyl malonate was added to the nonaqueous electrolytic solution in place of methyl 2-(methanesulfonyloxy)propionate thereto, and the battery was evaluated. The result is shown in Table 1.

TABLE 1

| | Composition of Electrolyte Salt Composition of Non-Aqueous Electrolytic Solution | Compound | Amount Added (wt %) | Discharge Capacity Retention Rate (%) after 50 cycles at 0° C. | Discharge Capacity Retention Rate (%) after 100 cycles at 60° C. |
|---|---|---|---|---|---|
| Example 1 | 1M LiPF6 EC/MEC/DEC(30/35/35) | methyl 2-(methanesulfonyloxy)propionate | 0.1 | 75 | 73 |
| Example 2 | 1M LiPF6 EC/MEC/DEC(30/35/35) | methyl 2-(methanesulfonyloxy)propionate | 1 | 83 | 84 |
| Example 3 | 1M LiPF6 EC/MEC/DEC(30/35/35) | methyl 2-(methanesulfonyloxy)propionate | 5 | 81 | 83 |
| Example 4 | 1M LiPF6 EC/MEC/DEC(30/35/35) | methyl 2-(methanesulfonyloxy)propionate | 10 | 79 | 78 |
| Example 5 | 1M LiPF6 EC/MEC/DEC(30/35/35) | methyl 2-(formyloxy)propionate | 1 | 80 | 81 |
| Example 6 | 1M LiPF6 EC/MEC/DEC(30/35/35) | 2-propenyl 2-(methanesulfonyloxy)propionate | 1 | 83 | 85 |
| Example 7 | 1M LiPF6 EC/MEC/DEC(30/35/35) | 2-propenyl 2-(formyloxy)propionate | 1 | 81 | 82 |
| Example 8 | 1M LiPF6 EC/MEC/DEC(30/35/35) | 2-propynyl 2-(methanesulfonyloxy)propionate | 1 | 85 | 87 |
| Example 9 | 1M LiPF6 EC/MEC/DEC(30/35/35) | 2-propynyl 2-(formyloxy)propionate | 1 | 83 | 83 |
| Example 10 | 1M LiPF6 EC/MEC/DEC(30/35/35) | methyl methanesulfonyloxyacetate | 1 | 86 | 87 |

TABLE 1-continued

| | Composition of Electrolyte Salt Composition of Non-Aqueous Electrolytic Solution | Compound | Amount Added (wt %) | Discharge Capacity Retention Rate (%) after 50 cycles at 0° C. | Discharge Capacity Retention Rate (%) after 100 cycles at 60° C. |
|---|---|---|---|---|---|
| Example 11 | 1M LiPF6 EC/MEC/DEC(30/35/35) | methyl formyloxyacetate | 1 | 83 | 84 |
| Example 12 | 1M LiPF6 EC/MEC/DEC(30/35/35) | methyl 2-(methanesulfonyloxy)-2-methylpropionate | 1 | 82 | 82 |
| Example 13 | 1M LiPF6 EC/MEC/DEC(30/35/35) | methyl 2-(formyloxy)-2-methylpropionate | 1 | 79 | 80 |
| Example 14 | 1M LiPF6 EC/MEC/DEC(30/35/35) | dimethyl 2,3-di(methanesulfonyloxy)succinate | 1 | 85 | 87 |
| Example 15 | 1M LiPF6 EC/MEC/DEC(30/35/35) | dimethyl 2,3-di(formyloxy)succinate | 1 | 84 | 85 |
| Example 16 | 0.95M LiPF6 + 0.05M LiN(SO2CF3)2 EC/VC/MEC/DEC (23/2/50/25) + 1,3-propanesulfone: 1 wt % | methyl 2-(methanesulfonyloxy)propionate | 1 | 85 | 87 |
| Example 17 | 0.95M LiPF6 + 0.05M LiBF4 FEC/PC/MEC/DMC (20/5/50/25) | methyl 2-(methanesulfonyloxy)propionate | 1 | 84 | 86 |
| Comparative Example 1 | 1M LiPF6 EC/MEC/DEC(30/35/35) | none | — | 61 | 59 |
| Comparative Example 2 | 1M LiPF6 EC/MEC/DEC(30/35/35) | dimethyl malonate | 1 | 64 | 57 |

Example 18

A positive electrode sheet was produced, using LiFePO$_4$ (positive electrode active material) in place of the positive electrode active material used in Example 2. 90% by mass of LiFePO$_4$ and 5% by mass of acetylene black (electroconductive agent) were mixed, and added to and mixed with a solution previously prepared by dissolving 5% by mass of polyvinylidene fluoride (binder) in 1-methyl-2-pyrrolidone, thereby preparing a positive electrode mixture paste. A cylindrical battery was produced and evaluated in the same manner as in Example 2, for which, however, the positive electrode mixture paste was applied onto an aluminium foil (collector), dried, processed under pressure and cut into a predetermined size, thereby producing a long rectangular, positive electrode sheet, and the final charging voltage was 3.6 V and the final discharging voltage was 2.0 V. The result is shown in Table 2.

Example 19

A negative electrode sheet was produced, using Si (negative electrode active material) in place of the negative electrode active material used in Example 2. 80% by mass of Si and 15% by mass of acetylene black (electroconductive agent) were mixed, and added to and mixed with a solution previously prepared by dissolving 5% by mass of polyvinylidene fluoride (binder) in 1-methyl-2-pyrrolidone, thereby preparing a negative electrode mixture paste. A cylindrical battery was produced in the same manner as in Example 2, for which, however, the negative electrode mixture paste was applied onto a copper foil (collector), dried, processed under pressure and cut into a predetermined size, thereby producing a long rectangular, negative electrode sheet; and the battery was evaluated. The result is shown Table 3.

Comparative Example 3

A cylindrical battery was produced in the same manner as in Example 18, for which, however, methyl 2-(methanesulfonyloxy)propionate was not added to the nonaqueous electrolytic solution; and the battery was evaluated. The result is shown in Table 2.

Comparative Example 4

A cylindrical battery was produced in the same manner as in Example 19, for which, however, methyl 2-(methanesulfonyloxy)propionate was not added to the nonaqueous electrolytic solution; and the battery was evaluated. The result is shown Table 3.

TABLE 2

| | Composition of Electrolyte Salt Composition of Non-Aqueous Electrolytic Solution | Compound | Amount Added (wt %) | Discharge Capacity Retention Rate (%) after 50 cycles at 0° C. | Discharge Capacity Retention Rate (%) after 100 cycles at 60° C. |
|---|---|---|---|---|---|
| Example 18 | 1M LiPF6 EC/MEC/DEC(30/35/35) | methyl 2-(methanesulfonyloxy)propionate | 1 | 84 | 86 |
| Comparative Example 3 | 1M LiPF6 EC/MEC/DEC(30/35/35) | none | 1 | 61 | 67 |

TABLE 3

|  | Composition of Electrolyte Salt Composition of Non-Aqueous Electrolytic Solution | Compound | Amount Added (wt %) | Discharge Capacity Retention Rate (%) after 50 cycles at 0° C. | Discharge Capacity Retention Rate (%) after 100 cycles at 60° C. |
|---|---|---|---|---|---|
| Example 19 | 1M LiPF6 EC/MEC/DEC(30/35/35) | methyl 2-(methanesulfonyloxy)propionate | 1 | 75 | 65 |
| Comparative Example 4 | 1M LiPF6 EC/MEC/DEC(30/35/35) | none | 1 | 57 | 30 |

All the lithium secondary batteries in Examples 1 to 17 have drastically improved low-temperature and high-temperature cycle property, as compared with the lithium secondary battery in Comparative Example 1 in which the hydroxy acid derivative compound of the present invention was not added, and that in Comparative Example 2 in which dimethyl malonate with two same substituents (carboxylate groups) bonded via a hydrocarbon group was added. It has been known that the structure with two different substituents, a carboxylate group (—CO$_2$R$^1$) and a sulfonyloxy group (—OSO$_2$R$^5$) or formyloxy group (—OCHO) bonded via a hydrocarbon group brings about the unexpected specific effect.

From comparison between Example 18 and Comparative Example 3, and from comparison between Example 19 and Comparative Example 4, the same effect is known also in the case of using a lithium-containing olivine-type phosphate for the positive electrode and in the case of using Si for the negative electrode. Accordingly, it is obvious that the effect of the present invention does not depend on a specific positive electrode or negative electrode.

In addition, it has been confirmed that the lithium primary battery that comprises a non-aqueous electrolytic solution containing the hydroxy acid derivative compound of the present invention is excellent in the low-temperature and high-temperature discharge performance after long-term storage.

INDUSTRIAL APPLICABILITY

The lithium battery comprising the nonaqueous electrolytic solution of the present invention is excellent in the low-temperature and high-temperature cycle property and can maintain an excellent battery performance for a long period of time.

The novel hydroxy acid derivative compound of the present invention is useful as intermediate materials for medicines, agricultural chemicals, electronic materials, polymer materials and the like, and as battery materials.

The invention claimed is:

1. A nonaqueous electrolytic solution comprising an electrolyte salt dissolved in a nonaqueous solvent, which contains at least one hydroxy acid derivative compound represented by the following general formulae (I) and (II) in an amount of from 0.01 to 10% by mass of the nonaqueous electrolytic solution:

[Formula 1]

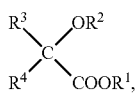
(I)

-continued

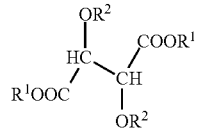
(II)

(in the general formulae (I) and (II), R$^1$ represents a linear or branched alkyl group having from 1 to 6 carbon atoms, a linear or branched alkenyl group having from 2 to 6 carbon atoms, or a linear or branched alkynyl group having from 3 to 6 carbon atoms; R$^2$ represents a sulfonyl group (—SO$_2$R$^5$) (where R$^5$ represents a linear or branched alkyl group having from 1 to 6 carbon atoms, or a linear or branched alkyl group having from 1 to 6 carbon atoms in which at least one hydrogen atom is substituted with a halogen atom), or a formyl group (—CHO); R$^3$ and R$^4$ each represent a hydrogen atom or a methyl group).

2. The nonaqueous electrolytic solution according to claim 1, wherein the hydroxy acid derivative compound of the general formula (I) is present and is one or more selected from methyl methanesulfonyloxyacetate, 2-propenyl methanesulfonyloxyacetate, 2-propynyl methanesulfonyloxyacetate, methyl formyloxyacetate, 2-propenyl formyloxyacetate, 2-propynyl formyloxyacetate, methyl 2-(methanesulfonyloxy)propionate, 2-propenyl 2-(methanesulfonyloxy)propionate, 2-propynyl 2-(methanesulfonyloxy)propionate, methyl 2-(formyloxy)propionate, 2-propenyl 2-(formyloxy)propionate, and 2-propynyl 2-(formyloxy)propionate.

3. The nonaqueous electrolytic solution according to claim 1, wherein the compound of the general formula (II) is present and is one or more selected from dimethyl 2,3-di(methanesulfonyloxy)succinate, di(2-propenyl) 2,3-di(methanesulfonyloxy)succinate, di(2-propynyl) 2,3-di(methanesulfonyloxy)succinate, dimethyl 2,3-di(formyloxy)succinate, di(2-propenyl) 2,3-di(formyloxy)succinate, and di(2-propynyl) 2,3-di(formyloxy)succinate.

4. The nonaqueous electrolytic solution according to claim 1, wherein the nonaqueous solvent comprises a cyclic carbonate and a linear carbonate.

5. The nonaqueous electrolytic solution according to claim 4, wherein the ratio (by volume) of cyclic carbonate/linear carbonate is from 10/90 to 40/60.

6. The nonaqueous electrolytic solution according to claim 4, wherein the cyclic carbonate comprises one or more selected from ethylene carbonate, propylene carbonate, butylene carbonate, 4-fluoro-1,3-dioxolan-2-one, trans or cis-4,5-difluoro-1,3-dioxolan-2-one, vinylene carbonate and vinylethylene carbonate.

7. The nonaqueous electrolytic solution according to claim 4, wherein the linear carbonate comprises one or more selected from asymmetric linear carbonates selected from methyl ethyl carbonate, methyl propyl carbonate, methyl isopropyl carbonate, methyl butyl carbonate and ethyl propyl carbonate, and symmetric linear carbonates selected from dimethyl carbonate, diethyl carbonate, dipropyl carbonate and dibutyl carbonate.

8. The nonaqueous electrolytic solution according to claim 1, wherein the electrolyte salt is one or more selected from $LiPF_6$, $LiBF_4$, $LiN(SO_2CF_3)_2$ and $LiN(SO_2C_2F_5)_2$.

9. The nonaqueous electrolytic solution according to claim 1, wherein a concentration of the electrolyte salt as dissolved in the solution is 0.3 to 2.5 M.

10. A lithium battery comprising a positive electrode, a negative electrode and a nonaqueous electrolytic solution of an electrolyte salt dissolved in a nonaqueous solvent, wherein the nonaqueous electrolytic solution contains at least one hydroxy acid derivative compound represented by the following general formulae (I) and (II) in an amount of from 0.01 to 10% by mass of the nonaqueous electrolytic solution:

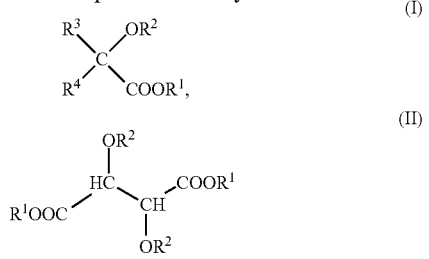

(in the general formulae (I) and (II), $R^1$ represents a linear or branched alkyl group having from 1 to 6 carbon atoms, a linear or branched alkenyl group having from 2 to 6 carbon atoms, or a linear or branched alkynyl group having from 3 to 6 carbon atoms; $R^2$ represents a sulfonyl group ($-SO_2R^5$) (where $R^5$ represents a linear or branched alkyl group having from 1 to 6 carbon atoms, or a linear or branched alkyl group having from 1 to 6 carbon atoms in which at least one hydrogen atom is substituted with a halogen atom), or a formyl group (—CHO); $R^3$ and $R^4$ each represent a hydrogen atom or a methyl group).

11. The lithium battery according to claim 10, wherein the positive electrode active material of the positive electrode is a complex metal oxide of lithium containing any of cobalt, manganese or nickel.

12. The lithium battery according to claim 11, wherein the complex metal oxides is one or more selected from $LiCoO_2$, $LiMn_2O_4$, $LiNiO_2$, $LiCo_{1-x}Ni_xO_2(0.01<x<1)$, $LiCo_{1/3}Ni_{1/3}Mn_{1/3}O_2$, $LiNi_{1/2}Mn_{3/2}O_4$ and $LiCo_{0.98}Mg_{0.02}O_2$.

13. The lithium battery according to claim 10, wherein the negative electrode active material of the negative electrode is one or more selected from lithium metal, lithium alloys, carbon materials, tin, tin compounds, silicon, silicon compounds capable of absorbing and releasing lithium.

* * * * *

UNITED STATES PATENT AND TRADEMARK OFFICE
CERTIFICATE OF CORRECTION

PATENT NO.       : 8,580,429 B2                                               Page 1 of 1
APPLICATION NO. : 12/921894
DATED            : November 12, 2013
INVENTOR(S)      : Abe et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 538 days.

Signed and Sealed this

Twenty-second Day of September, 2015

Michelle K. Lee
*Director of the United States Patent and Trademark Office*